United States Patent [19]

Ranalletta et al.

[11] Patent Number: 5,196,025

[45] Date of Patent: Mar. 23, 1993

[54] LANCET ACTUATOR WITH RETRACTABLE MECHANISM

[75] Inventors: Joseph V. Ranalletta, Guntersville; Fred E. Williams, Jr., Arab, both of Ala.

[73] Assignees: Ryder International Corporation, Arab, Ala.; Boehringer Mannheim Corporation, Indianapolis, Ind. ; a part interest

[21] Appl. No.: 526,290

[22] Filed: May 21, 1990

[51] Int. Cl.$^5$ ................................................ A61B 5/00
[52] U.S. Cl. .................................... 606/182; 606/185; 128/770
[58] Field of Search ................ 606/181, 182; 128/770; 604/136, 192-198

[56] References Cited

U.S. PATENT DOCUMENTS

| 2,061 | 4/1841 | Osdel ................................ 606/182 |
| 4,450 | 4/1846 | Gemrig . |
| 55,620 | 6/1866 | Capewell . |
| 245,040 | 7/1977 | Thomas . |
| 677,756 | 7/1901 | Caldwell . |
| 1,135,465 | 4/1915 | Pollock . |
| 2,694,398 | 11/1954 | LaDrigue . |
| 2,864,370 | 9/1955 | Alvos . |
| 3,358,689 | 12/1967 | Higgins . |
| 3,659,608 | 5/1972 | Perry . |
| 3,741,197 | 6/1973 | Sanz et al. . |
| 3,760,809 | 9/1973 | Campbell . |
| 3,903,887 | 9/1975 | Antoshkiw . |
| 4,078,552 | 3/1978 | Chen et al. . |
| 4,139,011 | 2/1979 | Benoit et al. . |
| 4,203,446 | 5/1980 | Hofert et al. . |
| 4,230,118 | 10/1980 | Holman et al. . |
| 4,358,539 | 11/1982 | Bittings . |
| 4,375,815 | 3/1983 | Burns . |
| 4,379,456 | 4/1983 | Cornell et al. . |
| 4,388,925 | 6/1983 | Burns . |
| 4,414,975 | 11/1983 | Ryder et al. . |
| 4,449,529 | 5/1984 | Burns et al. . |
| 4,452,243 | 6/1984 | Leopoldi et al. . |
| 4,455,510 | 6/1984 | Rigby . |
| 4,469,110 | 9/1984 | Slama . |
| 4,628,929 | 12/1986 | Intengan et al. . |
| 4,735,203 | 4/1988 | Ryder et al. . |
| 4,892,097 | 1/1990 | Ranalletta et al. . |
| 4,924,879 | 5/1990 | O'Brien ............................... 606/182 |
| 5,035,704 | 7/1991 | Lambert et al. .................... 606/182 |

Primary Examiner—John D. Yasko
Assistant Examiner—William W. Lewis
Attorney, Agent, or Firm—Trexler, Bushnell, Giangiorgi & Blackstone, Ltd.

[57] ABSTRACT

The present invention provides an actuator mechanism for sequentially advancing and retracting a lancet needle and includes a drive carriage for advancing and retracting the lancet needle and a hinge structure operatively connected to displace the drive carriage. The hinge structure includes first and second coupled leaf members relatively pivotal between a first position thereof in which the drive carriage is advanced to project and thrust the lancet needle into a tissue penetration position, and the second pivotal position of the leaf members in which the drive carriage is retracted to withdraw the lancet needle from the penetration position. The leaf members can also be pivotal to a third position in which the drive carriage is retracted prior to initiating the advancement so that the first position of the leaf members is pivotally intermediate between the second and third relative positions thereof. The drive carriage is thus advanced and thereafter retracted for thrusting and then withdrawing the lancet needle in continuous reversal motions thereof. The drive carriage is guided so that the advancement and retraction motions are along a highly accurate linear path.

30 Claims, 2 Drawing Sheets

LANCET ACTUATOR WITH RETRACTABLE MECHANISM

BACKGROUND OF THE INVENTION

This invention relates to lancet devices for use by physicians and technicians to extract a patient's blood sample, and more particularly relates to a mechanism for effecting the initial puncture and thereafter retracting the lancet needle following the skin puncturing procedure.

In order to reduce trauma to the patient during blood sampling procedures, automated finger lancet devices have been developed which eliminate the patient's view of both skin puncture and the lancet needle or blade itself. As described for example in U.S. Pat. No. 4,892,097, the lancet needle can be housed within a small device which provides a spring-driven mechanism for thrusting and retracting the needle. While such devices obstruct the patient's view, considerable patient discomfort has been experienced when all lateral motion of the lancet needle is not prevented. This disadvantage is eliminated by the lancet actuator in accordance with the present invention which provides improved patient comfort in that initial puncture and withdrawal of the lancet needle is effected in a continuous, smooth motion, and this is done rapidly, so that little or no lateral movement can take place.

SUMMARY OF THE INVENTION

In accordance with the present invention, an actuator mechanism for sequentially advancing and retracting a lancet needle includes a drive carriage for advancing and retracting the lancet needle and a hinge structure operatively connected to displace the drive carriage. The hinge structure includes first and second coupled leaf members relatively pivotal between a first position thereof in which the drive carriage is advanced to project and thrust the lancet needle into a tissue penetration position, and the second pivotal position of the leaf members in which the drive carriage is retracted to withdraw the lancet needle from the penetration position. The leaf members can also be pivotal to a third position in which the drive carriage is retracted prior to initiating the advancement so that the first position of the leaf members is pivotally intermediate between the second and third relative positions thereof. The drive carriage is thus advanced and thereafter retracted for thrusting and then withdrawing the lancet needle in continuous reversal motions thereof. The drive carriage is guided so that the advancement and retraction motions are long a highly accurate linear path.

In a preferred embodiment, the drive carriage is integrally molded with a double hinge structure to form a transmission linkage including two "living hinge" portions which convert the radial motion of the leaf members into the linear motions of the drive carriage and lancet needle. The smoothly guided and highly accurate linear motions of the lancet needle reduce the user discomfort. The drive carriage accepts removable lancet needle units so that the actuator is reusable with successive lancet needles. The actuator includes trigger and rearming structures which tension and release a torsion spring bearing against one of the leaf members to drive the transmission linkage and actuator operation.

A second preferred embodiment of the actuator is designed for single-use disposability, in which the lancet needle is insert molded within the drive carriage, and accordingly reuse of the unit by rearming or resetting of the structure is precluded.

DESCRIPTION OF THE ILLUSTRATED EMBODIMENT

Figure 1:
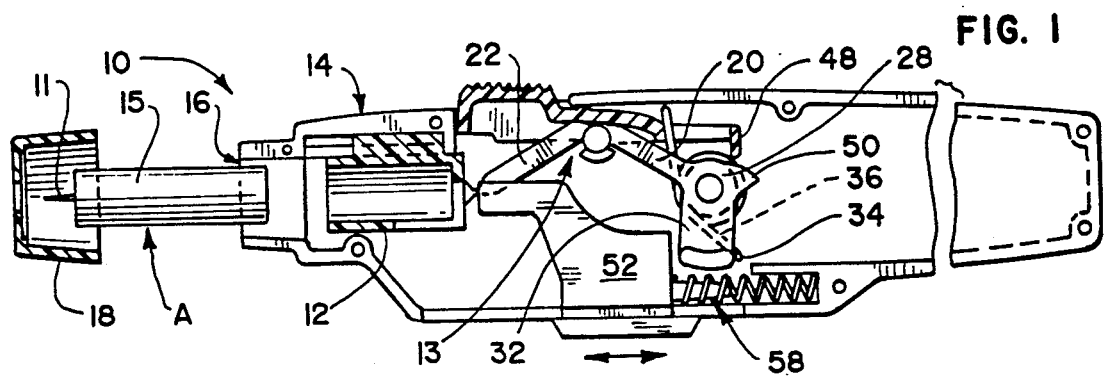
FIG. 1 is a cross-sectional view of a first embodiment of a lancet actuator device in accordance with the present invention.

Referring to FIG. 1, an embodiment of a lancet actuator in accordance with the present invention is generally designated by reference character 10. The actuator 10 accommodates the use of conventional, disposable lancet needle-and-support-body units A. The units A comprise a metal needle 11 carried by a plastic body 15. A lancet unit A is inserted into a lancet holder or carriage means 12 within the actuator 10, as more fully described hereinafter, prior to operation of the actuator 10 to puncture tissue in a blood sample extraction procedure, after which the lancet unit A is removed from the holder or carriage 12 for disposal. In the actuator 10 of the first embodiment, a split housing 14 has an access and operation aperture 16 formed at one end, through which the disposable lancet unit A is inserted and removed. The actuator 10 also has a cap 18 which is snap-fitted to the housing 14 to cover the aperture 16 and the inserted lancet unit A during the blood extraction procedure, and therefore the cap 18 will be exposed to the blood sample and will consequently be disposable with the used lancet unit A. The cap 18 includes an opening 18a through which the needle 11 of lancet A can project. The extension of the cap 18 determines the length of the projection of the needle portion 11 therefrom, and therefore also determines the puncture depth when the cap 18 is seated on the donor's skin. FIG. 1 illustrates the mechanism of the actuator 10 preparatory to insertion of the lancet unit A and before the actuating mechanism has been cocked to prepare the actuator for operation. As can be appreciated, this condition of the actuator 10 also corresponds to that as would occur after completion of a prior procedure. Thus, the lancet unit A is positioned within the carriage or holder 12 and the cap 18 is snapped into place. The actuator is then cocked to arrive at the position shown in FIG. 2, as explained more fully hereinafter, and is thus ready for operation.

Figure 2:
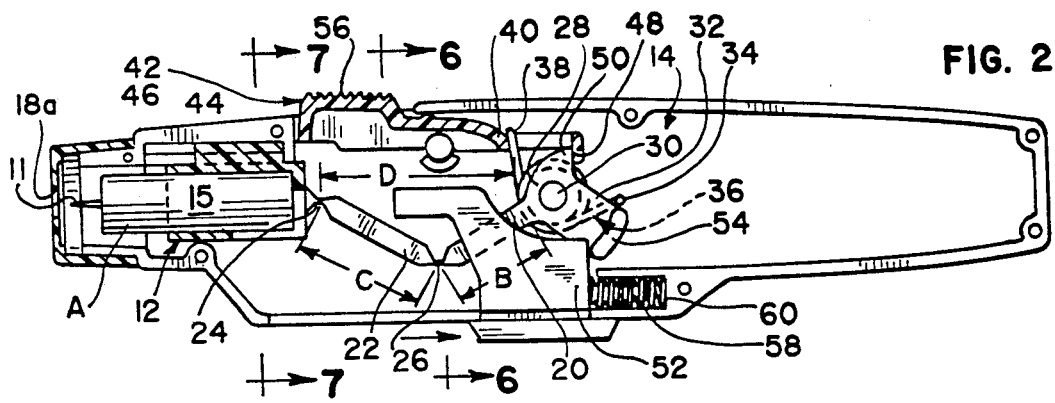
FIGS. 2-4 are sectional views similar to FIG. 1 illustrating sequential operating positions of the actuator mechanism of the device.
Figure 3:
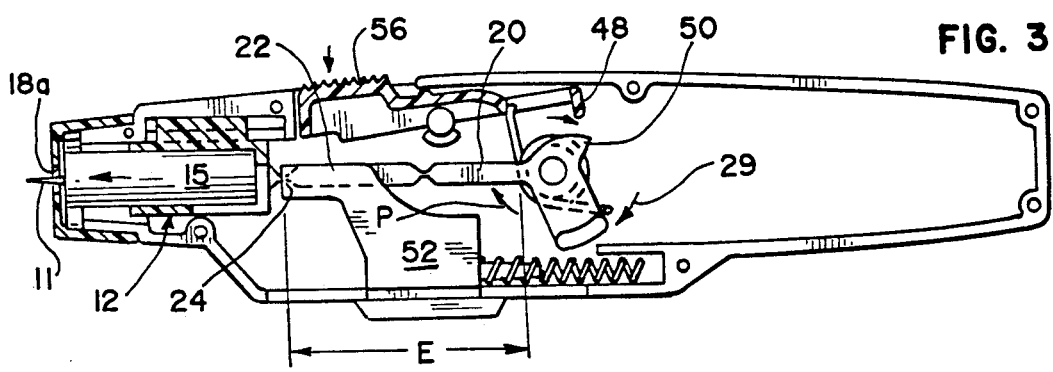
Figure 4:
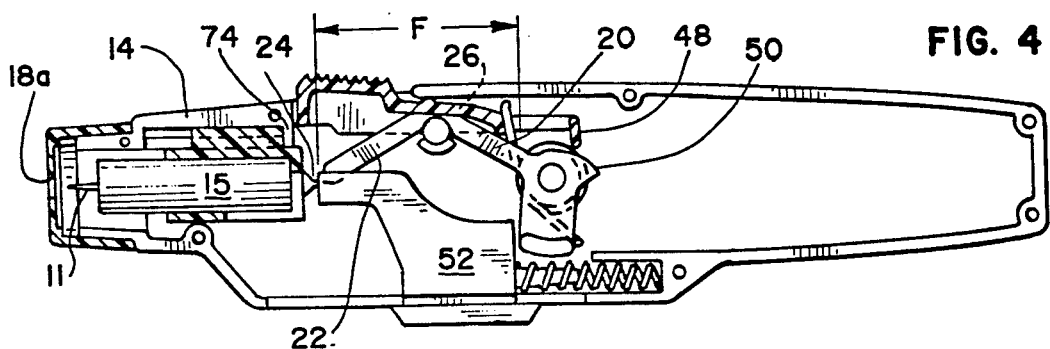

In operation of the actuator 10, the lancet holder 12 carries the lancet unit A from the retracted position shown in FIG. 2 to the linearly advanced position shown in FIG. 3 in which the lancet needle 11 projects from the clearance hole 18a to puncture the tissue, and then immediately retracts the lancet unit A into the position shown in FIG. 4. FIGS. 1 and 4 illustrate the same retracted position of the holder 12, although FIG. 1 also shows the cap 18 and lancet unit A prior to assembly.

The holder or carriage 12 is integrally molded and connected with a double hinge linkage structure 13 including first and second hinge leaf members 20 and 22 respectively, which form a transmission linkage to convert the radial motion of the leaf members 20 and 22 into linear motion of the holder or carriage 12 and the associated lancet unit A. The second leaf 22 is directly coupled to the rear wall of the carriage 12 by a first integrally attenuated, flexible pivot portion 24 forming a "living hinge" at the forward end of the second leaf member 22. A second integrally attenuated flexible portion 26 forms a "living hinge" joining the rear end of the second leaf 22 to the forward end of the first leaf 20 enabling relative pivot of the two leaves 20 and 22. A rotatable hub 28 is integrally molded at the rear end of the first leaf member 20. The first leaf 20 pivots with the rotation of the hub 28, as indicated by arrow 29, FIG. 3, which hub 28 is journaled on a stationary pivot bearing pin 30 which projects inwardly from the housing half 14. The hub 30 has a radially projecting boss 32 which seats the movable end 34 of a torsion spring 36 which is wound around the hub 30 and drives the hub rotation in the lancet displacement operation. The generally anchored end 38 of the torsion spring 36 is seated against a spring seat portion 40 of a pivoted trigger member, generally designated by reference character 42. The trigger member 42 has an integral pivot bearing pin 44 which is pivotally supported on an arcuate journal bearing 46 which projects inwardly from the housing half 14. The interior end of the trigger 42 is formed as a latch portion 48 which releasably engages a retainer cam 50 projecting from the hub 28 as shown in FIG. 2. The releasable trigger latching of the cam 50 retains the tension in the torsion spring 36 which maintains force against both the boss 32 and the trigger seat 40 in the cocked or armed condition of the actuator 10 shown in FIG. 2.

In order to arm the actuator 10 from the released condition of the spring 36 or previously fired position as shown in FIG. 1 in which the latch 48 is disengaged from the cam 50, a displaceable cocking member 52 is slidably mounted as shown for rearward movement into engagement with a laterally projecting foot portion 54 formed on the end of the boss 32. The cocking, counter-rotation of the foot 54 and hub 28 continue until the cam 50 reaches the latch 48, which is under tension from the spring 36. The element or cam 50 will pivot the latch position 48 of trigger 42 upwardly, until said latch portion engages over the cam 50, to attain the armed or cocked position as shown in FIG. 2.

The rearward cocking motion of the cocking member 52 also compresses an attached, biasing coil spring 58 within a blind guide bore 60 formed in the housing 14. When this cocking motion is completed, manual disengagement from the cocking member 52 will permit the biasing spring 58 to return the cocking member 52 to a neutral position (FIGS. 1, 3 and 4) in which the biasing spring 58 is in expanded condition. Comparison of FIGS. 1 and 2 illustrates that the counterclockwise cocking motion of the hub 28 pivots the first leaf member 20 and the second hinge portion 26 downwardly as indicated by the motion arrows in FIG. 2.

Figure 6:
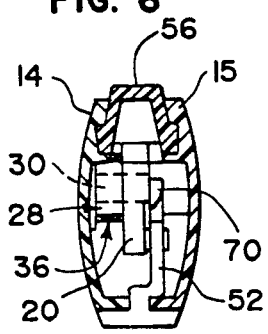
FIG. 6 is a sectional view along a plane indicated at line 6—6 in FIG. 2.
Figure 7:
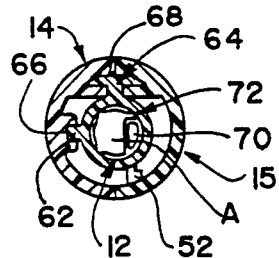
FIG. 7 is a sectional view along a plane indicated at line 7—7 in FIG. 2.

At the other end of the integral linkage structure 13, as best shown in FIG. 6, the holder or carriage 12 has a laterally projecting and longitudinally extending guide flange 62 and an upwardly projecting and similarly longitudinally extended guide flange 64 which has a modified dove-tail or similarly convoluted cross-sectional configuration; the two guide flanges 62 and 64 are slidably displaceable through corresponding, mating receiving slots formed in the housing halves 14 and 15. FIG. 7 also illustrates that the slot 68 is vertically split between the housing halves 14 and 15. The guide flanges 62 and 64 insure that the holder 12 and lancet unit A are displaceable only in a smooth and accurately linear longitudinal path during advancement and retraction, without any lateral motion so that the lancet needle 11 enters and withdraws from the skin at a highly focused point of penetration, which eliminates any side-to-side motion of the lancet needle and the resulting penetration trauma and user discomfort experienced with prior actuator devices.

Since the holder or carriage 12 is constrained to an accurately linear longitudinal path of the advancement and retraction, the first hinge portion 24 adjacent the rear wall of the holder 12 is similarly limited to the highly linear motion of the holder displacement; therefor the downwardly pivotal motion of the second hinge portion 26 about the pin 30 pulls the rear end of the leaf 22 downwardly to induce a combined pivot and rearward translation of the leaf 22 which also pulls the rearward retraction of the holder 12 and lancet unit A through the highly linear path constrained by the guide flanges 62 and 64. FIG. 2 illustrates the pivotal position of the leaf members 20 and 22 which retracts the holder 12 into its "armed position" prepared for advancement, in which the hinge portion 24 is a distance D from the surface of the rotatable hub 28, which is determined in general by the lengths B and C of the respective leaf members 20 and 22 and the angle of relative pivot therebetween.

Referring again to FIG. 3, when the surface of the cap 18 is placed against the donor's arm, and the trigger surface 56 is manually depressed the latch 48 is disengaged from the cam 50 and the hub 28 rotates in a clockwise direction, as indicated by arrow 29, under the influence of spring 36 to begin the lancet needle and skin puncture procedure. As hub 28 rotates, the leaf member 20 is pivotally driven upwardly and clockwise as indicated by the direction of the arrow P. Correspondingly, the leaf 22 will pivot in a counterclockwise direction from the position shown in FIG. 2 to the intermediate position of FIG. 3. The resulting pivotal movement of the coupled leaf member 22 produces the linear advancement of the holder or carriage 12 and lancet needle 11 which reaches its maximum projection from the cap aperture 18a (corresponding to the maximum skin puncture depth) when the leaf members 20 and 22 are linearly aligned, as shown in FIG. 3, corresponding to the position of hinge portion 24 at maximum distance E from the surface of the hub 28. Thus, the advancing displacement of the holder 12 and lancet needle 11 can be expressed by the difference between the distance E and the distance D. In addition, however, the torsion spring 36 continues to drive the hub 28, which produces continued upward, clockwise pivotal movement of the leaf member 20 so that the resulting pivot of the leaf member 22, in which hinge portion 26 becomes elevated relative to the hinge portion 24, produces a smooth reversal in the advancement of the holder or carriage 12 and lancet needle 11 and their linear withdrawal to the maximum position of retraction shown in FIG. 4 which is indicated by the position of the hinge portion 24 at minimum distance F from the surface of the hub 28. This reverse stroke of the holder and lancet needle can be expressed by the difference between the distance E and the distance F.

The operation of the actuator 10 from the armed position in FIG. 2 through the intermediate, skin puncturing position in FIG. 3 and continuously to the needle withdrawal, retracted position in FIG. 4 can thus be measured by the displacements of the hinge portion 24 from the initially retracted distance D to the maximally advanced distance E and then retracted to the distance F in the smooth and highly linear displacement reversals as the leaf member 20 is pivotally driven clockwise by the tensioned torsion spring 36.

Figure 5:
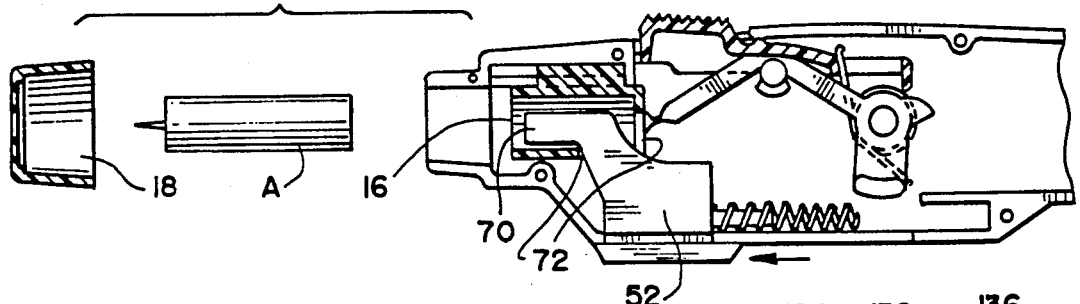
FIG. 5 is a fragmentary sectional view similar to FIGS. 1-4 and illustrating removal of a lancet unit from the device.

When the actuator operation and lancet puncture procedure are completed as reflected in the actuator position shown in FIG. 4, the used lancet unit A is ejected from the holder 12 by sliding the cocking member 52 forward from its neutral position as shown in FIG. 4 into the forward position shown in FIG. 5; in this position the ejector portion 70, on the upper part of the cocking member 52 enters and passes through the slot 72 formed through the rear end of the holder so that the ejector portion 70 engages and displaces the lancet unit A from the aperture 16 of the holder 12. The cocking member 52 is then manually retracted to the neutral position shown in FIG. 4 so that the ejector portion 70 is withdrawn from the slot 72. A new lancet unit A can then be inserted into the holder 12 which is maintained in the fully retracted position of FIG. 4 during the friction-fit insertion of the lancet unit A by a stop member 74, depending from the housing 14. The stop member 74 engages the rear end of the guide flange 64 to arrest further retraction of the holder 12. After installing the new lancet unit A, the actuator 10 can then be armed to the position shown in FIG. 2 in the cocking operation described hereinabove with reference thereto.

Figure 8:
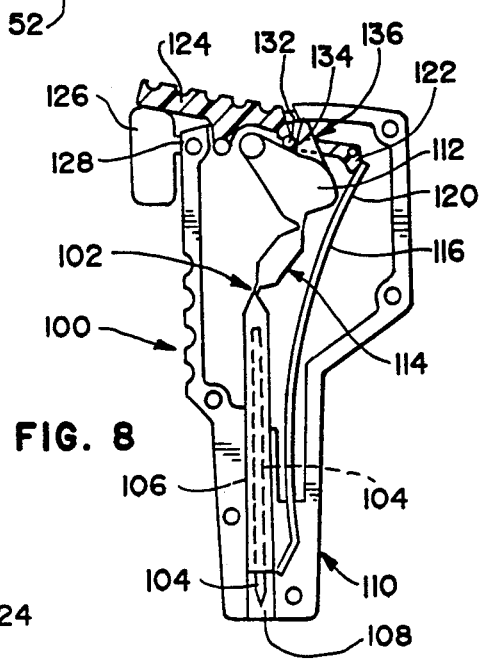
FIGS. 8-10 are cross-sectional views of sequential operating positions of an actuator mechanism within a second embodiment of the lancet actuator device in accordance with the present invention.
Figure 9:
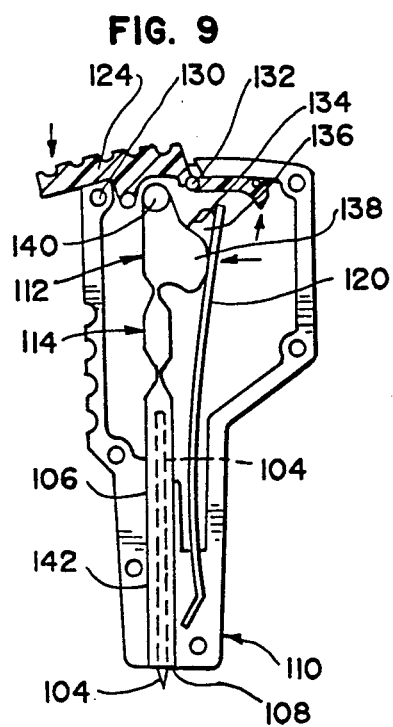
Figure 10:
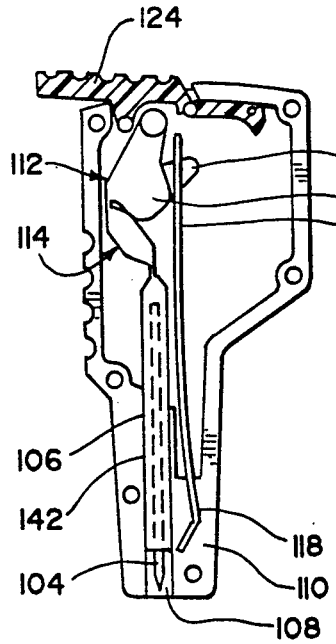

Referring now to FIGS. 8, 9 and 10, a second embodiment of the actuator in accordance with this invention is generally designated by reference character 100. The entire actuator 100 can be employed for single-use disposability, and therefore the double hinged linkage structure generally designated by reference character 102 is similar to the double hinge linkage structure 13 in the first embodiment of the actuator 10, with the exception that a lancet needle 104 is insert molded within the integrally molded holder or carriage 106.

In operation, the lancet needle 104 is driven forwardly from the retracted position shown in FIG. 8 to project from the operation aperture 108 at the forward end of the split housing 110 as shown in FIG. 9; the continued pivot of the first and second leaf members 112 and 114 of the linkage structure 102 produces the immediately sequential retraction of the lancet needle 104 and holder 106 to the safely withdrawn position shown in FIG. 10. The operation of the actuator is driven by a flat or leaf spring 116 which is anchored at one end 118 within the housing 110 and is initially flexed as shown in FIG. 8 by engagement of the opposite end 120 against a spring seat 122 formed at the rear end of a manual trigger member 124. The trigger member 124 is maintained in the armed condition of the actuator 100 and spring 116 by wedged engagement with a safety tab 126 which is integrally secured to the housing 110 by a small detachable web 128.

When the actuator 100 is employed to puncture the intended tissue, the web 128 is fractured to detach the safety tab 126. After removal of the safety tab 126, the trigger member 124 can be manually depressed in a downward direction as shown in FIG. 9, thus pivoting the trigger member about the pivot bearing 130 so that the spring end 120 becomes unseated from the trigger spring seat 122 and a retaining pin 132 on the trigger becomes unseated from a retaining notch 134 formed in a retaining cam 136 extending from the first leaf member 112. The released spring end 120 unflexes leftwardly, as shown in FIG. 9, so that it engages against a bearing cam 138 formed on the first leaf member 112 so that the entire leaf member 112 is driven to pivot in a clockwise direction about the integrally formed pivot bearing 140 which is journaled in the housing 110. Resulting relative pivotal motion of the hinge members 112 and 114 brings the hinge members to the intermediate position of full extension as shown in FIG. 9 which advances the integrally hinged holder or carriage 106 slidably through the extended guide bore 142 formed in the housing 110. The bore 142 opens into the operating aperture 108 from which the advanced lancet needle 104 is extended to achieve the tissue puncture. Thereafter as shown in FIG. 10 the continuous clockwise rotation of the first leaf member 112 under action of the spring end 120 also drives the smoothly continuous relative pivot of the second leaf member 114 which pulls the immediately sequential and highly accurate linear retraction of the holder 106 through the guide bore 142 as shown in FIG. 10 so that the lancet needle is safely withdrawn from the aperture 108. Since the second actuator embodiment 100 has a simplified design for single-use disposability, a rearming mechanism for repeated use is unnecessary but could be provided.

In light of the foregoing description of the embodied lancet actuators, modifications will be evident to those skilled in the design of such mechanisms and are within the broad scope of the appended claims and equivalents thereof.

We claim:

1. A mechanism for sequentially advancing and retracting a lancet needle, comprising:
   (a) drive carriage means for carrying, advancing, and retracting the lancet needle;
   (b) a hinge structure operatively connected to linearly displace said drive carriage means on a linear path along an axis of said drive carriage means and including first and second coupled leaf members, said drive carriage means being connected to one of said first and second leaf members which are relatively pivotal between a first position thereof in which said drive carriage means is advanced to project and thrust the lancet needle into a tissue penetration position and a second position in which said drive carriage means is retracted from said advance to withdraw the lancet needle from the penetration position the other of said first and second leaf members being further coupled to a pivot bearing structure of said mechanism for supporting said relative pivot.

2. A mechanism according to claim 1, wherein said leaf members are relatively pivotal to a third position thereof in which said drive carriage means is retracted prior to initiating said advancement to said first position.

3. A mechanism according to claim 2, wherein said first position of said leaf members is pivotally intermediate between said second and third relative positions thereof.

4. A mechanism according to claim 1, further comprising control means for actuating relative pivotal movement of said leaf members from said third position through said first position into said second position such that said drive carriage means is advanced and thereafter retracted for thrusting and then withdrawing said lancet needle in continuous motions thereof.

5. A mechanism according to claim 4, wherein said control means comprises energy storage means for propelling said relative pivotal motion of said first and second leaf members.

6. A mechanism according to claim 5, wherein said energy storage means comprises spring means bearing against said first leaf member and propelling pivotal movement thereof relative to said second leaf member.

7. A mechanism according to claim 1, further comprising guide means for guiding said advancement and retraction of said drive carriage means along a linear displacement path.

8. A mechanism according to claim 1, wherein said first and second leaf members are pivotally extended at an angle of 180. therebetween in said first position.

9. A mechanism according to claim 1, wherein said hinge structure includes a first pivot bearing means pivotally coupling said first and second leaf members, said first pivot bearing means being pivotal about a second pivot bearing means during said relative pivot of said first and second leaf members.

10. A mechanism according to claim 1, wherein said hinge structure further comprises a second, translationally stationary pivot bearing means secured to one end of said first leaf member and an opposite end of said first leaf member is secured to a first pivot bearing means pivotally coupling said first and second leaf members, said first pivot bearing means being pivotal about said second pivot bearing means during said relative pivot of said first and second leaf members between said first and second positions.

11. A mechanism according to claim 10, further comprising control means for actuating said pivot of said leaf members.

12. A mechanism according to claim 11, wherein said control means comprises spring means bearing against said first leaf member and propelling pivot thereof relative to said second leaf member.

13. A mechanism according to claim 12, wherein said control means further comprises retention means for releasably retaining energy of said spring means for said propulsion.

14. A mechanism according to claim 13, wherein said retention means comprises manually operable release means for releasing said spring means energy.

15. A mechanism according to claim 1, further comprising spring means bearing against said first leaf member for propelling pivot thereof relative to said second leaf member, and cocking means for energizing said spring means.

16. An actuating mechanism for sequentially advancing and retracting a lancet needle, comprising:
 a) drive carriage means for carrying, advancing, and retracting the lancet needle;
 b) a hinge structure operatively connected to displace said drive carriage means and including first and second coupled leaf members, said drive carriage means being connected to said second leaf member, said first and second leaf members being relatively pivotal between a first position thereof in which said drive carriage means is advanced to project and thrust the lancet needle into a tissue penetration position and a second position in which said drive carriage means is retracted from said advance to withdraw the lancet needle from the penetration position, wherein said hinge structure further comprises a second, translationally stationary pivot bearing means secured to one end of said first leaf member and an opposite end of said first leaf member is secured to a first pivot bearing means pivotally coupling said first and second leaf members, said first pivot bearing means being pivotal about said second pivot bearing means during said first and second positions and wherein said second pivot bearing means comprises a rotational hub member on which a torsion spring bears for propelling pivot of said first leaf member.

17. A mechanism according to claim 16, comprising control means for actuating rotation of said hub member and pivot of said first leaf member.

18. A mechanism according to claim 17, wherein said control means comprises manually operable trigger means for releasing tension in said torsion spring for said propulsion.

19. A mechanism according to claim 18, wherein said trigger means comprises a cam portion projecting from said hub member and releasably engaged by a deflectable trigger latch member for retaining said tension torsion spring until manual deflection of said trigger latch releases the engagement of said can and said tension.

20. An actuating mechanism for sequentially advancing and retracting a lancet needle, comprising:
 a) drive carriage means for carrying, advancing, and retracting the lancet needle;
 b) a hinge structure operatively connected to displace said drive carriage means and including first and second coupled leaf members, said drive carriage means being connected to said second leaf member, said first and second leaf members being relatively pivotal between a first position thereof in which said drive carriage means is advanced to project and thrust the lancet needle into a tissue penetration position and a second position in which said drive carriage means is retracted from said advance to withdraw the lancet needle from the penetration position, further comprising spring means bearing against said first leaf member for propelling pivot thereof relative to said second leaf member, and cocking means for energizing said spring means, wherein said cocking means is movably biased toward a neutral position thereof removed from energizing said spring means.

21. An actuating mechanism for sequentially advancing and retracting a lancet needle, comprising:
 a) drive carriage means for carrying, advancing, and retracting the lancet needle;
 b) a hinge structure operatively connected to displace said drive carriage means and including first and second coupled leaf members, said drive carriage means being connected to said second leaf member, said first and second leaf members being relatively pivotal between a first position thereof in which said drive carriage means is advanced to project and thrust the lancet needle into a tissue penetration position and a second position in which said drive carriage means is retracted from said advance to withdraw the lancet needle from the penetration position, wherein said hinge structure further comprises a pivot bearing rotational hub secured to one end of said first leaf member on which a spring means bears for propelling said pivot of said first leaf member, and further comprising a cocking member selectively engageable with either said hub for energizing said spring means, or engageable with said drive carriage means for detatchment of a lancet structure removably carried on said drive carriage means.

22. An actuating mechanism for sequentially advancing and retracting a lancet needle, comprising:
   a) drive carriage means for carrying, advancing, and retracting the lancet needle;
   b) a hinge structure operatively connected to displace said drive carriage means and including first and second coupled leaf members, said drive carriage means being connected to one of said first and second leaf members which are relatively pivotal between a first position thereof in which said drive carriage means is advanced to project and thrust the lancet needle into a tissue penetration position and a second position in which said drive carriage means is retracted from said advance to withdraw the lancet needle from the penetration position, the other of said first and second leaf members being further coupled to a pivot bearing structure of said mechanism, wherein said drive carriage means comprises a housing structure for removably receiving a body portion of a lancet structure, said body portion being slidably received and withdrawn through an access aperture formed in said housing structure.

23. A mechanism according to claim 22, wherein said drive carriage housing structure includes a through slot through which an ejection portion of said cocking member enters said housing structure and displaces said lancet structure therefrom through said access aperture in order to achieve said detachment of said lancet structure therefrom.

24. A mechanism according to claim 22, further comprising a housing for containing and supporting said mechanism, said housing having a stop member secured therein for engagement with said drive carriage housing structure at a terminally retracted position thereof in order to hold said drive carriage housing structure stationary during slidable insertion of said lancet body and structure therein.

25. A mechanism for sequentially advancing and retracting a lancet needle, comprising:
   a) drive carriage means for carrying, advancing, and retracting the lancet needle;
   b) a hinge structure operatively connected to displace said drive carriage means and including first and second coupled leaf members which are relatively pivotal between a first position thereof in which said drive carriage means is advanced to project and thrust the lancet needle into a tissue penetration position and a second position in which said drive carriage means is retracted from said advance to withdraw the lancet needle from the penetration position, wherein said drive carriage means and said first and second leaf members are integrally molded and defined within a unitary molded structure wherein said drive carriage means is connected to said second leaf member by a first attenuated portion of said molded structure forming a flexible hinge coupling between said second leaf member and said drive carriage means, and wherein said first and second leaf members are joined by a second attenuated portion of said unitary molded structure pivotally coupling said leaf members, said first leaf member being further coupled to a pivot bearing structure therefor, such that said relative pivot of said first and second leaf members produces said advancement and retraction of said integrally connected drive carriage means.

26. An actuating mechanism for sequentially advancing and retracting a lancet needle comprising:
   a) drive carriage means for carrying, advancing, and retracting the lancet needle;
   b) a hinge structure operatively connected to displace said drive carriage means and including first and second coupled leaf members relatively pivotal between a first position thereof in which said drive carriage means is advanced to project and thrust the lancet needle into tissue penetration position and a second position in which said drive carriage means is retracted to withdraw the lancet needle from the penetration position thereof, wherein said drive carriage means and said first and second leaf members are integrally molded and in which said drive carriage means is connected to one of said first and second leaf members by a first flexible hinge coupling portion, the other of said first and second leaf members being further coupled to a pivot bearing support therefor, and said first and second leaf members are joined by a second flexible hinge coupling portion such that relative pivot of said first and second leaf members produces said advancement and retraction of said integrally connected drive carriage means.

27. A mechanism according to claim 26, further comprising guide means for guiding said advancement and retraction of said drive carriage means along a highly linear displacement path.

28. A unitary, molded transmission linkage structure for use in sequentially advancing and retracting a lancet needle, comprising:
   a) drive carriage means for carrying, advancing, and retracting the lancet needle;
   b) a hinge structure operatively connected to displace said drive carriage means and including first and second coupled leaf members relatively pivotal between a first position thereof in which said drive carriage means is advanced to project and thrust the lancet needle into tissue penetration position and a second position in which said drive carriage means is retracted to withdraw the lancet needle from the penetration position thereof, wherein said drive carriage means and said first and second leaf members are integrally molded in which said drive carriage means is connected to one of said first and second leaf members by a first flexible hinge coupling portion, the other of said first and second leaf members being further coupled to a pivot bearing support therefor, and said first and second leaf members are joined by a second flexible hinge coupling portion such that relative pivot of said first and second leaf members produces said advancement and retraction of said integrally connected drive carriage means.

29. A unitary, molded transmission linkage structure according to claim 28, further comprising said lancet needle secured to said drive carriage means.

30. A unitary, molded transmission linkage structure according to claim 29, wherein said lancet needle is secured by insertion during said integral molding of said drive carriage means.

* * * * *